(12) United States Patent
Schaller et al.

(10) Patent No.: US 9,038,881 B1
(45) Date of Patent: May 26, 2015

(54) FEEDER BELT ACTUATION MECHANISM FOR TRUE MULTI-FIRE SURGICAL STAPLER

(75) Inventors: Michael P. Schaller, Palo Alto, CA (US); Philipe R. Manoux, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 1354 days.

(21) Appl. No.: 12/436,101

(22) Filed: May 5, 2009

(51) Int. Cl.
*A61B 17/068* (2006.01)
*A61B 17/064* (2006.01)
*A61B 17/072* (2006.01)

(52) U.S. Cl.
CPC ......... *A61B 17/064* (2013.01); *A61B 17/07207* (2013.01); *A61B 2017/07271* (2013.01)

(58) Field of Classification Search
CPC ........... A61B 17/07207; A61B 17/064; A61B 17/072; A61B 17/128; A61B 2017/07214; A61B 2017/07271
USPC ...................... 227/175.1–182.1, 19, 901, 902; 606/219
See application file for complete search history.

(56) References Cited

U.S. PATENT DOCUMENTS

| | | | | |
|---|---|---|---|---|
| 2,140,593 | A | * | 12/1938 | Pankonin ...................... 206/340 |
| 3,581,551 | A | | 6/1971 | Wilkinson |
| 3,650,453 | A | | 3/1972 | Smith, Jr. |
| 3,899,914 | A | | 8/1975 | Akiyama |
| 4,086,926 | A | | 5/1978 | Green |
| 4,228,895 | A | * | 10/1980 | Larkin ........................... 206/339 |
| 4,475,679 | A | | 10/1984 | Fleury, Jr. |
| 4,633,861 | A | | 1/1987 | Chow et al. |
| 4,762,260 | A | | 8/1988 | Richards et al. |
| 4,969,591 | A | | 11/1990 | Richards et al. |
| 5,156,315 | A | | 10/1992 | Green et al. |
| 5,192,288 | A | | 3/1993 | Thompson et al. |
| 5,413,272 | A | | 5/1995 | Green et al. |
| 5,476,206 | A | | 12/1995 | Green |
| 5,655,698 | A | | 8/1997 | Yoon |
| 5,662,260 | A | | 9/1997 | Yoon |
| 5,692,668 | A | | 12/1997 | Schulze et al. |

(Continued)

FOREIGN PATENT DOCUMENTS

| | | |
|---|---|---|
| EP | 1238634 | 9/1994 |
| JP | 2005160933 | 6/2005 |

(Continued)

OTHER PUBLICATIONS

Gong, Shao W., "Perfectly flexible mechanism and integrated mechanism system design", *Mechanism and Machine Theory* 39 (2004), (Nov. 2004),1155-1174.

(Continued)

*Primary Examiner* — Andrew M Tecco
(74) *Attorney, Agent, or Firm* — Womble, Carlyle, Sandridge & Rice

(57) ABSTRACT

One example of a surgical apparatus may include a feeder belt, a plurality of staples frangibly connected to the feeder belt, and at least one pull tab extending laterally from the feeder belt. An example of a surgical method of treating tissue within the body of a patient may include providing at least one feeder belt and staples frangibly connected thereto, and at least one wedge movable relative to the feeder belt; moving at least one wedge in a first direction to contact and thereby form and shear at least one staple from at least one feeder belt; and moving at least one wedge in a second direction to engage and advance the feeder belt.

11 Claims, 10 Drawing Sheets

(56) References Cited

U.S. PATENT DOCUMENTS

| | | | |
|---|---|---|---|
| 5,810,855 | A | 9/1998 | Rayburn et al. |
| 5,816,471 | A | 10/1998 | Plyley et al. |
| 5,855,311 | A | 1/1999 | Hamblin et al. |
| 5,894,979 | A | 4/1999 | Powell |
| 5,918,791 | A | 7/1999 | Sorrentino et al. |
| 5,964,774 | A | 10/1999 | McKean et al. |
| 6,306,149 | B1 | 10/2001 | Meade |
| 6,391,038 | B2 | 5/2002 | Vargas et al. |
| 6,602,252 | B2 | 8/2003 | Mollenauer |
| 6,716,232 | B1 | 4/2004 | Vidal et al. |
| 6,817,508 | B1 | 11/2004 | Racenet et al. |
| 6,843,403 | B2 | 1/2005 | Whitman |
| 6,994,714 | B2 * | 2/2006 | Vargas et al. ............... 606/153 |
| 7,025,747 | B2 | 4/2006 | Smith |
| 7,097,089 | B2 | 8/2006 | Marczyk |
| 7,140,527 | B2 | 11/2006 | Ehrenfels et al. |
| 7,168,604 | B2 | 1/2007 | Milliman et al. |
| 7,172,104 | B2 | 2/2007 | Scirica et al. |
| 7,179,267 | B2 | 2/2007 | Nolan et al. |
| 7,207,471 | B2 | 4/2007 | Heinrich et al. |
| 7,213,736 | B2 | 5/2007 | Wales et al. |
| 7,225,963 | B2 | 6/2007 | Scirica |
| 7,225,964 | B2 | 6/2007 | Mastri et al. |
| 7,234,624 | B2 | 6/2007 | Gresham et al. |
| 7,238,195 | B2 | 7/2007 | Viola |
| 7,300,444 | B1 * | 11/2007 | Nielsen et al. ............... 606/153 |
| 2003/0120284 | A1 | 6/2003 | Palacios et al. |
| 2003/0236551 | A1 | 12/2003 | Peterson |
| 2005/0184121 | A1 | 8/2005 | Heinrich |
| 2006/0011699 | A1 | 1/2006 | Olson et al. |
| 2006/0041273 | A1 | 2/2006 | Ortiz et al. |
| 2006/0151567 | A1 | 7/2006 | Roy |
| 2007/0027472 | A1 | 2/2007 | Hiles et al. |
| 2007/0034668 | A1 | 2/2007 | Holsten et al. |
| 2007/0073341 | A1 | 3/2007 | Smith et al. |
| 2007/0083234 | A1 | 4/2007 | Shelton, IV et al. |
| 2007/0118163 | A1 | 5/2007 | Boudreaux et al. |
| 2007/0125828 | A1 | 6/2007 | Rethy et al. |
| 2009/0065552 | A1 * | 3/2009 | Knodel et al. ............. 227/180.1 |

FOREIGN PATENT DOCUMENTS

| | | | |
|---|---|---|---|
| RU | | 2080833 | 6/1997 |
| WO | | WO-81/01953 | 7/1981 |
| WO | | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Cardica Microcutter Implant Delivery Device 510(k), Cover Sheet, Table 10.1, "Substantial Equivalence Comparison," and Section 12, "Substantial Equivalence Discussion"".

* cited by examiner

FEEDER BELT ACTUATION MECHANISM FOR TRUE MULTI-FIRE SURGICAL STAPLER

FIELD OF THE INVENTION

The invention generally relates to surgical staples and stapling.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The surgeon inserts the endocutter through a trocar or other port or incision in the body, orients the end of the endocutter around the tissue to be transected, and compresses the anvil and cartridge together to clamp the tissue. Then, a row or rows of staples are deployed on either side of the transection line, and a blade is advanced along the transection line to divide the tissue.

During actuation of an endocutter, the cartridge fires all of the staples that it holds. In order to deploy more staples, the endocutter must be moved away from the surgical site and removed from the patient, after which the old cartridge is exchanged for a new cartridge. The endocutter is then reinserted into the patient. However, it can be difficult and/or time-consuming to located the surgical site after reinsertion. Further, the process of removing the endocutter from the patient after each use, replacing the cartridge, and then finding the surgical site again is tedious, inconvenient and time-consuming, particularly where a surgical procedure requires multiple uses of the endocutter. That inconvenience may discourage surgeons from using the endocutter for procedures in which use of an endocutter may benefit the patient. Similar inconveniences may accompany the use of surgical staplers other than endocutters.

BRIEF DESCRIPTION OF THE DRAWINGS

The use of the same reference symbols in different figures indicates similar or identical items.

DETAILED DESCRIPTION

U.S. patent application Ser. No. 11/851,379, filed Sep. 6, 2007; U.S. patent application Ser. No. 11/956,988, filed Dec. 14, 2007; U.S. patent application Ser. No. 12/263,171, filed Oct. 31, 2008 (the "Endocutter Documents") are hereby incorporated by reference herein in their entirety. The Endocutter Documents describe a surgical stapler that includes an end effector attached to a shaft, which in turn is attached to a handle. The Endocutter Documents also describe a feeder belt extending into the end effector, where staples extend from and are frangibly connected to the feeder belt.

Figure 1:
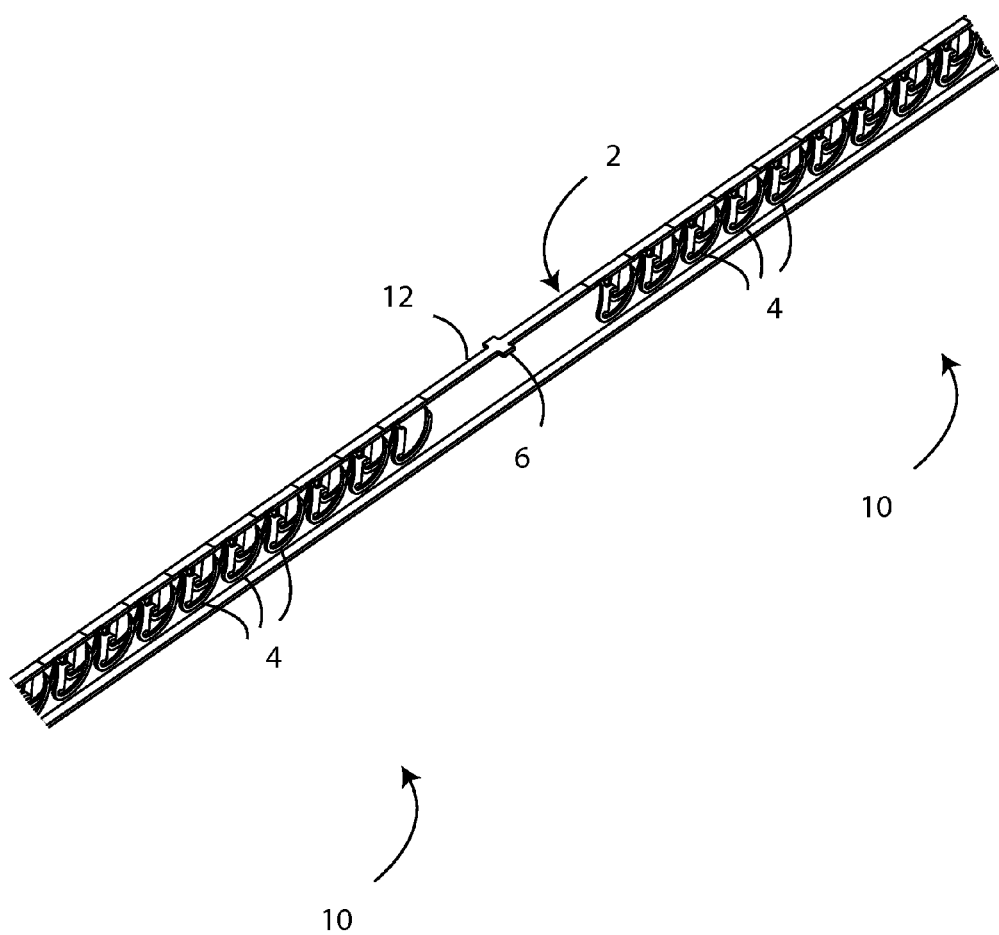
FIG. 1 is a perspective view of an exemplary feeder belt.

Referring to FIG. 1, a feeder belt 2 is provided, from which one or more staples 4 extend. A frangible connection between the feeder belt 2 and each corresponding staple 4 may be made in any suitable manner. The feeder belt 2 and staples 4 may be configured substantially as described in the Endocutter Documents. At least one pull tab 6 may extend laterally outward from at least one feeder belt 2 in at least one lateral direction. The tab 6 may extend laterally outward from the feeder belt 2 laterally both left and right, as shown in FIG. 1, or may extend laterally in only a single direction. The pull tab 6 may be longitudinally spaced apart from staples 4 proximal and/or distal to the pull tab 6. The pull tab 6 may be substantially the same thickness as the feeder belt 2.

One or more rows 8 of staples 4 may be connected to the feeder belt 2. Each row 8 of staples 4 is the group of staples 4 positioned at substantially the same lateral location relative to the longitudinal centerline of the feeder belt 2. At least two longitudinally-adjacent staples 4 in each row 8 may be spaced apart a distance different from the distance between two other longitudinally-adjacent staples 4. Consequently, the staples 4 in each row 8 may be grouped together in two or more separate groups 10. Each group 10 of staples 4 in a row 8 may be separated from a longitudinally adjacent group 10 of staples 4 by a blank space 12 on the feeder belt 2, where that blank space may have any suitable length. Advantageously, no staples 4 extend from, or into an area bounded by, the blank space 12 of the feeder belt 2. At least one pull tab 6 may be positioned in a blank space 12. Advantageously, a pull tab 6 is located in each blank space 12 between groups 10 of staples 4, and a pull tab 6 is located distal to the distalmost group 10 of staples 4 on the feeder belt 2.

Figure 2:
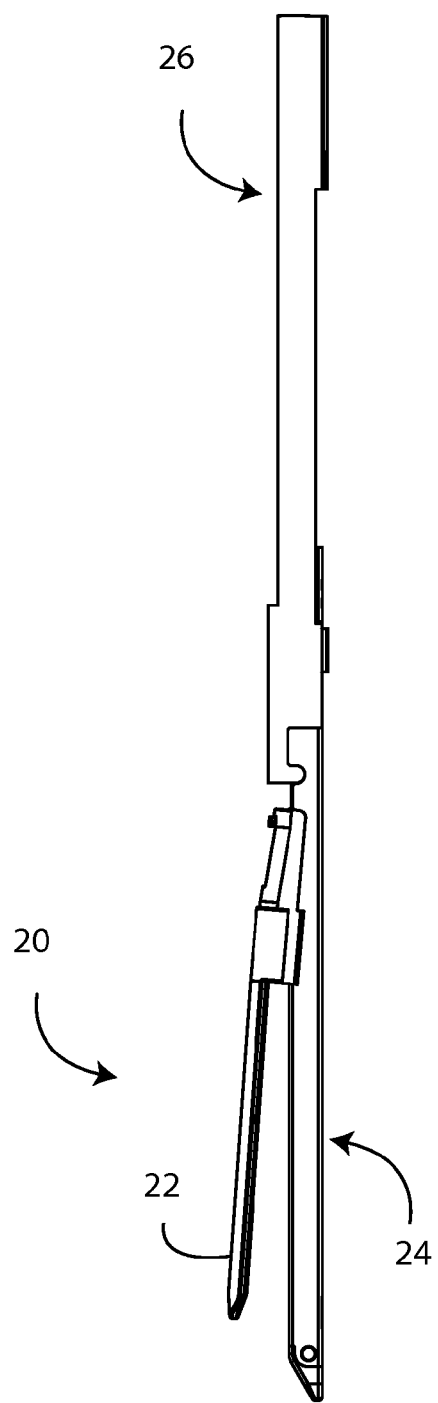
FIG. 2 is a side view of an exemplary end effector of a surgical stapler that utilizes the feeder belt of FIG. 1.
Figure 3:
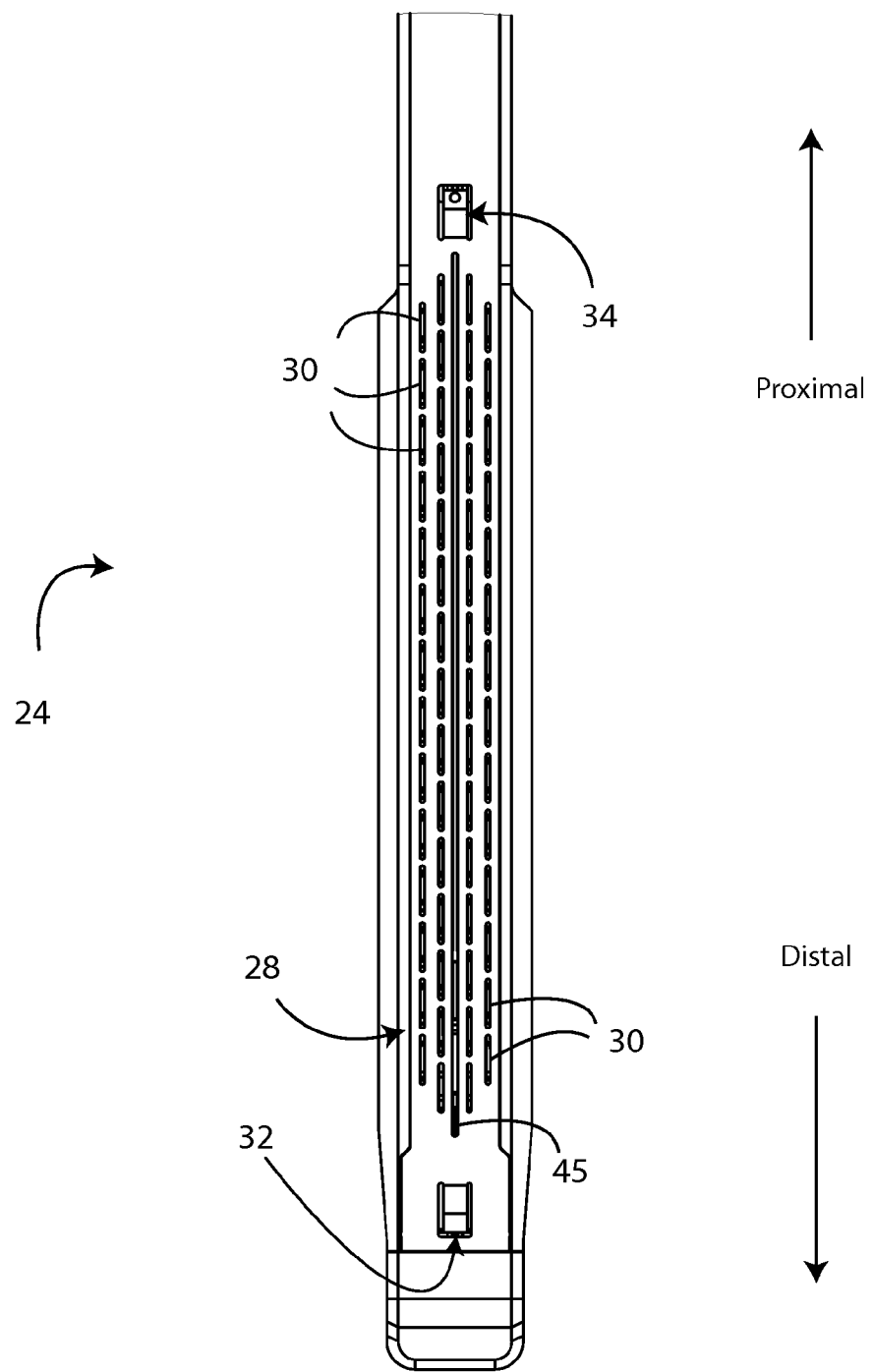
FIG. 3 is a top view of the staple holder of the end effector of FIG. 2.
Figure 5:
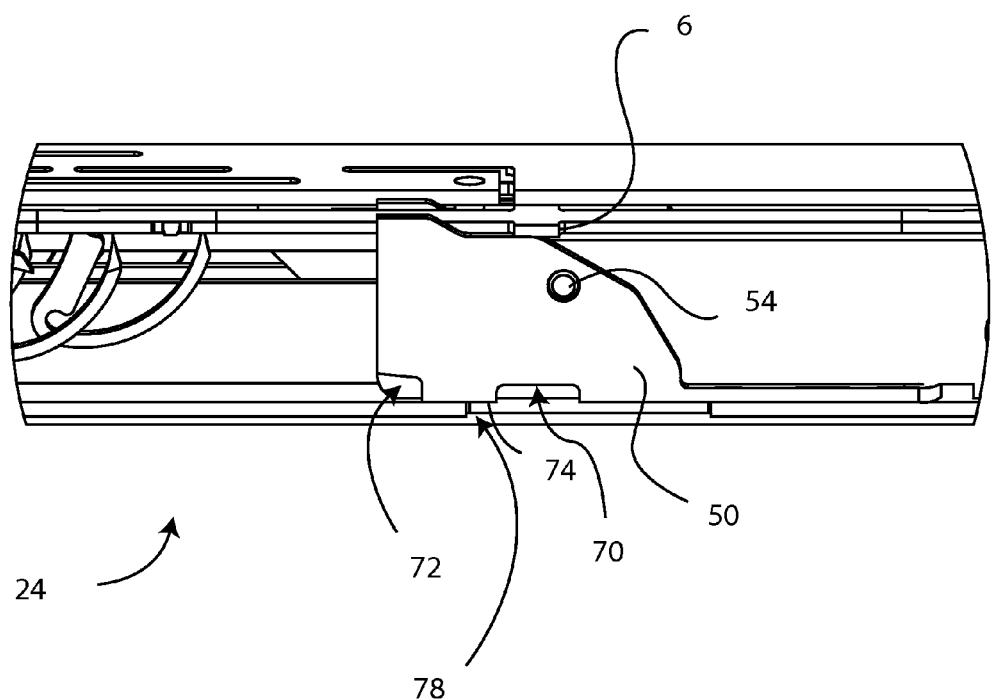
FIG. 5 is a side view of the actuation assembly of FIG. 4 in a first position within the staple holder of FIG. 3.
Figure 6:
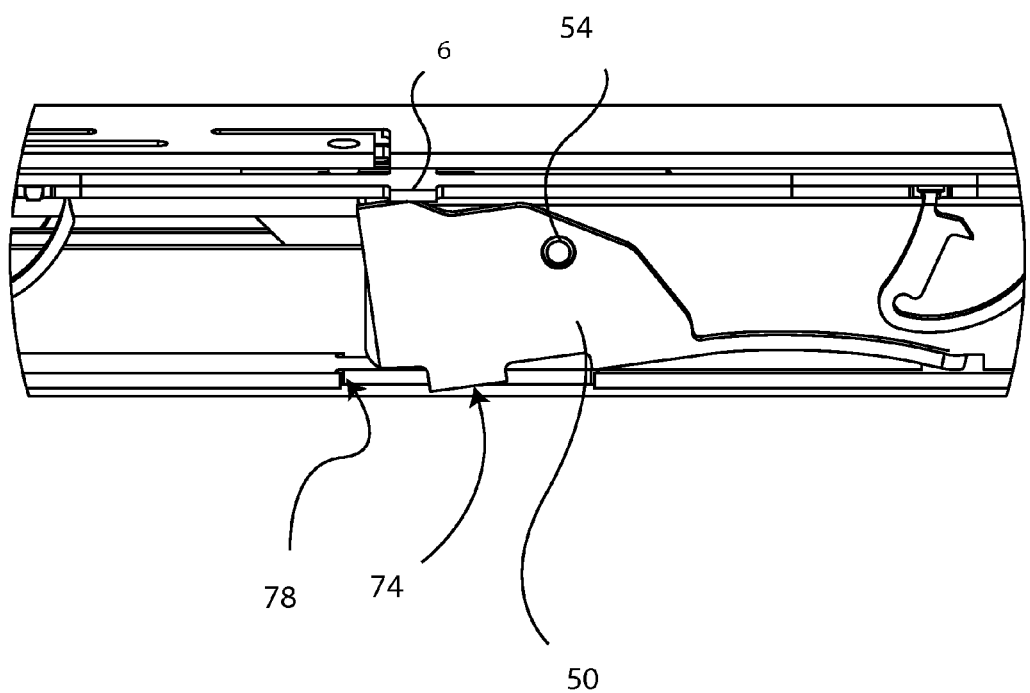
FIG. 6 is a side view of the actuation assembly of FIG. 4 in a second position within the staple holder of FIG. 3.
Figure 7:
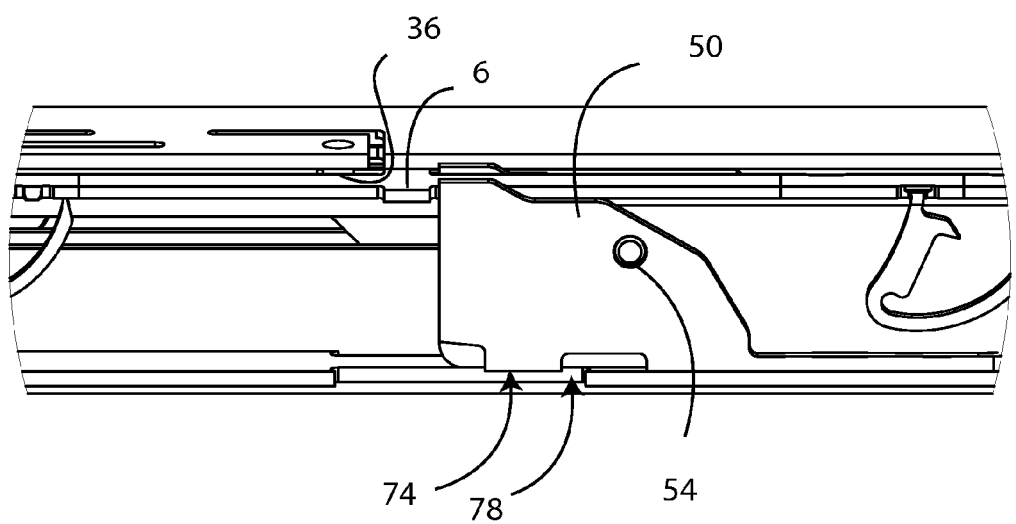
FIG. 7 is a side view of the actuation assembly of FIG. 4 in a third position within the staple holder of FIG. 3.

Referring also to FIG. 2, the end effector 20 may include a staple holder 24 and an anvil 22 positioned at the distal end of a shaft 26. One or more feeder belts 2 extend into a space defined within the staple holder 24, such as set forth in the Endocutter Documents. Referring also to FIG. 3, a thin piece of material may be an upper plate 28 of the staple holder 24. The upper plate 28 of the staple holder 24 may includes a number of apertures 30 defined therethrough. The apertures 30 are aligned with the positions of the corresponding staples 4 in the staple holder 24, such that staples 4 are deployed out of the staple holder 24 through the apertures 30. A tensioning tab 32 may be defined in the upper plate 28 of the staple holder 24. The proximal end of the tensioning tab 32 may be fixed to the upper plate 28 of the staple holder 24, and the distal end of the tensioning tab 32 may be free and biased downward into the staple holder 24. A stop tab 34 may be defined in the upper plate 28 of the staple holder 24. Referring also to FIGS. 5-7, the distal end of the stop tab 34 may be fixed to the upper plate 28 of the staple holder 24, and the proximal end of the stop tab 34 may be free and biased downward into the staple holder 24.

A post 36 may be defined on the lower surface of the stop tab 34 near the proximal end of the stop tab 34. Alternately, the post 36 may be located at a different position on the stop tab 34, or may be omitted altogether.

Figure 4:
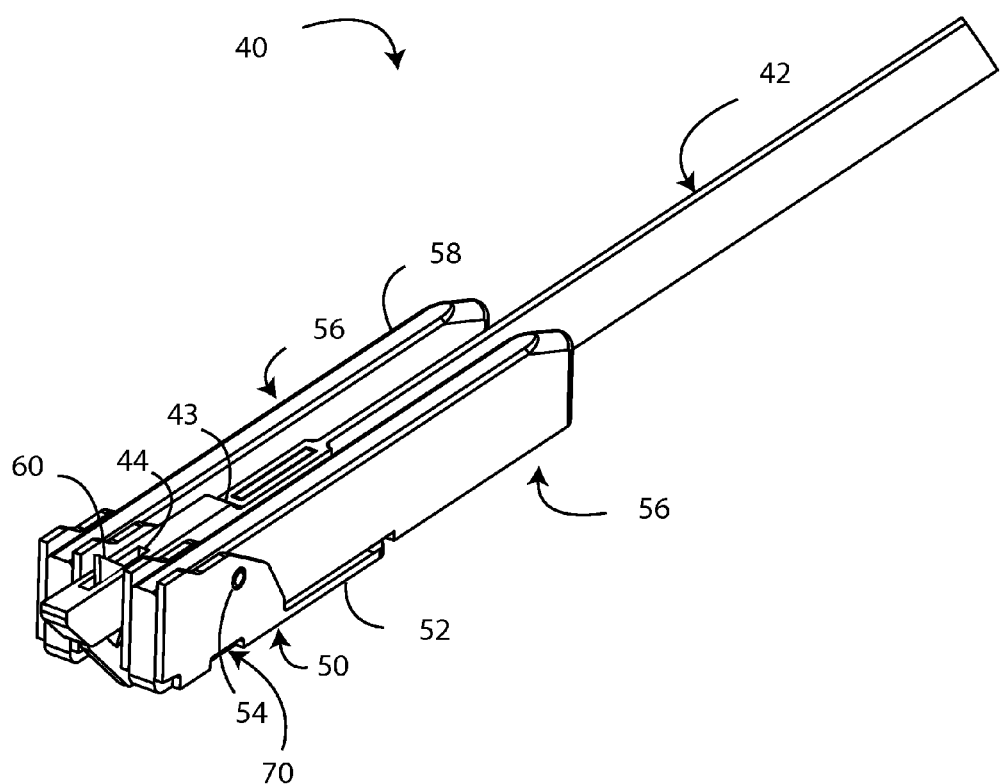
FIG. 4 is a perspective view of an actuation assembly.

Referring also to FIG. 4, an actuation assembly 40 also may extend into a space defined within the staple holder 24. The actuation assembly 40 may include a drive bar 42 that may extend proximally out of the staple holder 24, or that may be held entirely within the staple holder 24 and also be connected to a control member (not shown) extending into the shaft 26. The drive bar 42 may be substantially rigid, and may have any suitable shape. An aperture 44 may be defined on an upper surface of the drive bar 42. The drive bar 42 may include a ramp 43 along its upper surface extending downward in the proximal direction, where the ramp 43 is located proximal to the aperture 44, and where the ramp 43 connects a higher surface at the distal end of the drive bar 42 to a lower surface of the drive bar 42 proximal to the ramp 43.

Lateral to the drive bar 42, on one or both sides of the drive bar 42, the actuation assembly 40 includes at least one wedge 50. Each wedge 50 is laterally positioned relative to the drive bar to encounter a row 8 of staples 4 during actuation of the drive bar 42, as described in greater detail below. At least one wedge 50 may be generally parallel to the drive bar 42. Advantageously, the wedges 50 may be generally parallel to one another. A wedge arm 52 may extend proximally from the wedge 50, from a lower surface of the wedge 50. The wedge arm 52 may be generally long and thin. Alternately, the wedge arm 52 may be shaped or configured differently, or may be omitted altogether. The wedge 50 may be shaped substantially as set forth in the Endocutter Documents, or may be shaped in any other suitable manner for engaging and deploying staples 4. Each wedge 50 may be connected to the drive bar 42 in any suitable manner. As one example, a pin 54 may extend through the drive bar 42 and be received by an aperture in the wedge 50. The wedge 50 may be freely rotatable about the pin 54, and/or the pin 54 may be freely rotatable relative to the drive bar 42. The pin 54 may extend through the drive bar 42 and through or into all of the wedges 50. Alternately, multiple pins 54 may be used. The ends of the pin 54 may be enlarged in diameter in order to retain the pin 54 within the actuation assembly 40 and prevent it from sliding out of the actuation assembly 40. The location of the pin 54 relative to the wedge 50 is selected to facilitate bending of the wedge arm 52 and rotation of the wedge 50, as described in greater detail below. Referring also to FIG. 5, the underside of the wedge 50 may include a center notch 70 defined therein. The underside of the wedge 50 may also, or instead, include a proximal notch 72 defined therein. Between the notches 70, 72 is a resulting protrusion 74 having a proximal end and a distal end. The wedge 50 and wedge arm 52 may be fabricated from any suitable material, including superelastic material such as nicklel-titanium alloy and plastically deformable material such as stainless steel.

Where the feeder belt 2 includes two rows 8 of staples 4, and two feeder belts 2 are utilized, one feeder belt 2 may be placed in the staple holder 24 on either side of the drive bar 42. Thus, advantageously two wedges 50 are positioned on either side of the drive bar 42. Those wedges 50 may be separated by a belt support 56, such that one belt support 56 is provided on each side of the drive bar 42. Each belt support 56 has a generally flat upper surface 58 across a portion of its length. The upper surface 58 may be substantially the same width as the feeder belt 2, or slightly narrower than the feeder belt 2. The upper surface 58 supports the feeder belt 2 during staple formation, and assists in constraining the vertical motion of the feeder belt 2 during staple formation, as described in greater detail below. The upper surface 58 of each belt support 56 may be angled or curved downward in the proximal direction at its proximal end. The belt supports 56 may be connected to the drive bar via a pin 54, or in any other suitable manner.

Figure 8:
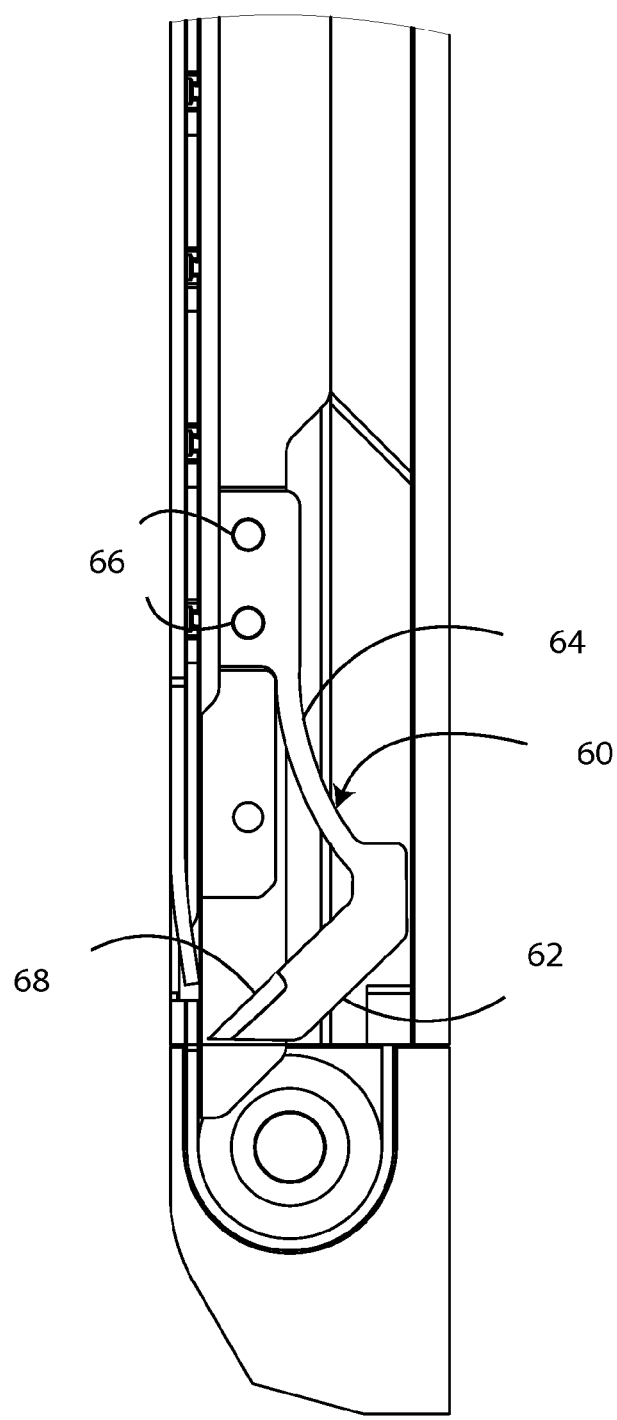
FIG. 8 is a side view of the knife of the actuation assembly of FIG. 4 in a first position within the staple holder of FIG. 3.

Referring also to FIG. 8, a cutter 60 may be fixed to the drive bar 42. The cutter 60 may be flexible, such as described in U.S. patent application Ser. No. 12/435,653, filed on May 5, 2009 (the "Knife Document"), which is hereby incorporated by reference in its entirety. The cutter 60 may include a knife 62 at the distal end of an arm 64. The arm 64 may be fixed to the drive bar 42 in any suitable manner. As one example, the arm 64 may include two apertures 66 configured to engage two corresponding posts in an inner volume of the drive bar 42. The posts may be molded into those apertures 66, or otherwise engage the apertures. The arm 64 may instead be fixed to the drive bar 42 in any other suitable manner. The cutter 60 may be in its neutral state as shown in FIG. 8, where the knife 62 and the cutting edge 68 of the knife 62 are located below the upper plate 28 of the staple holder 24. Alternately, the cutter 60 may not be in the neutral state as shown in FIG. 8, and instead may be held in that position in any suitable manner. As described in greater detail below, the knife 62 and cutting edge 68 move upward through the aperture 44 in the drive bar 42 and out of the upper plate 28 of the staple holder 24 to cut tissue during actuation of the staple holder 24. The pin or pins 54 are configured to ensure that the knife 62 is movable in that manner without engaging the pin or pins 54 and being prevented from moving upward. Alternately, the cutter 60 may be configured in any other suitable manner.

Operation

Actuation of the feeder belt 2 may be performed as described in the Endocutter Documents, or in any other suitable manner, as modified by the description below. The end effector 20 is introduced into the patient, and is closed onto tissue. The end effector 20 is then actuated to deploy the staples 4 into tissue. The actuation assembly 40 is initially located in an initial position in a distal region of the staple holder 24. The actuation assembly 40 is pulled proximally in order to deploy staples 4 and cut tissue, to a final position. The actuation assembly 40 is then moved distally back to the initial position before the next firing.

Proximal force is applied to the drive bar 42. As the drive bar 42 moves proximally, it pulls the wedges 50 proximally. As set forth in the Endocutter Documents, each wedge 50 encounters staples 4 in a row 8 one after the other, and drives those staples 4 into tissue, deforms them, and shears them from the feeder belt 2. The drive bar 42 also pulls the belt supports 56 proximally. The feeder belt 2 corresponding to each belt support 56 is constrained vertically between the upper surface 58 of the belt support 56 and the lower surface of the upper plate 28, which may be only slightly greater than the thickness of the feeder belt 2. In this way, lateral twisting, longitudinal bowing and other deformations of the feeder belt 2 during firing of the staples 4 is minimized. Further, any deformation of the feeder belt 2 resulting from its advancement into the staple holder 24 may be smoothed by entry of that feeder belt 2 into the constrained space between the upper surface 58 of the belt support 56 and the lower surface of the upper plate 28. As the belt support 56 and corresponding wedges 50 slide proximally, the two may remain substantially fixed in position relative to one another, such that the belt support 56 supports the feeder belt 2 longitudinally relative to the wedges in the same manner throughout travel of the actuation assembly.

Figure 10:
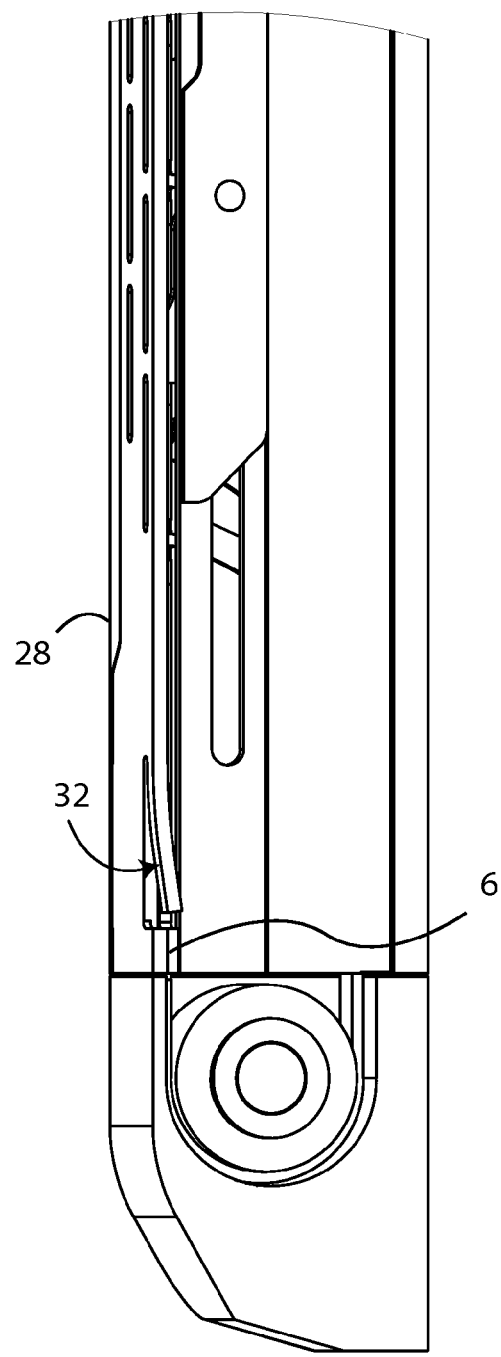
FIG. 10 is a side view of a tensioning tab of the staple holder of FIG. 3 engaging the feeder belt of FIG. 1.

Further, referring to FIG. 10, prior to actuation of the actuation assembly 40 and firing of the staples, the tensioning tab 32 is biased downward into the staple holder 24, as described above. The free end of the tensioning tab 32 is located proximal to, and is adjacent to, a corresponding pull tab 6 of at least one feeder belt 2. Where two feeder belts 2 are used, the tensioning tab 32 is advantageously wide enough to engage pull tabs 6 of both feeder belts 2, and those pull tabs 6 are oriented such that the tensioning tab 32 can do so. As the actuation assembly 40 moves proximally and the wedges 50 begin to contact and deform the staples, the wedges 50 exert a force on the feeder belt 2 that has a component in the proximal direction. That proximal force pulls the pull tab 6 located distal to the tensioning tab 32 into contact with the tensioning tab 32, such that the tensioning tab 32 prevents proximal motion of the pull tab 6 and therefore restrains the feeder belt 2 against proximal motion. In this way, the proximal motion of the wedges 50 causes tensioning of the feeder belt 2. That tension, and/or the constraint of the feeder belt 2 vertically between the upper surface 58 of the belt support 56 and the lower surface of the upper plate 28, holds the feeder belt 2 in place during firing of the staples 4, such that the feeder belt 2 need not be clamped as set forth in the Endocutter Documents. Optionally, the feeder belt 2 also may be clamped, if desired.

Figure 9:
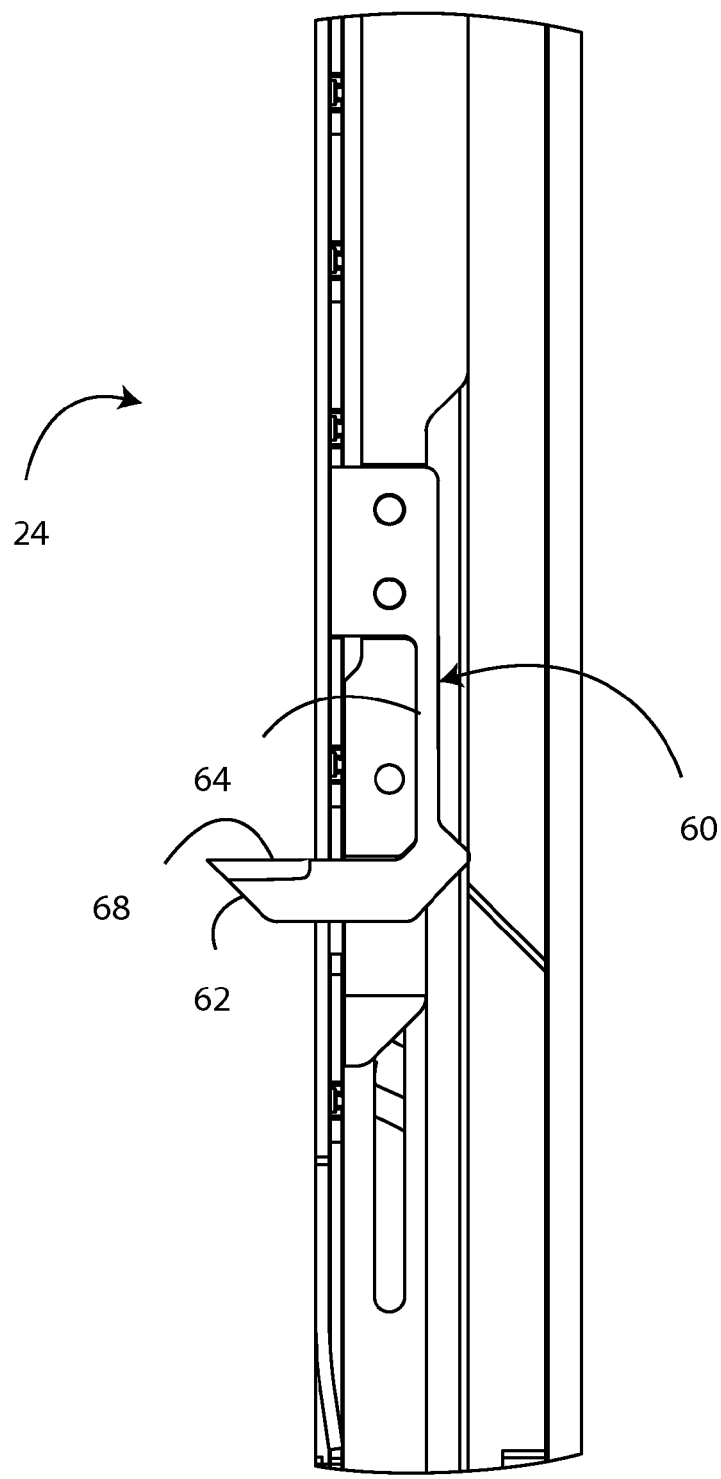
FIG. 9 is a side view of the knife of the actuation assembly of FIG. 4 in a second position within the staple holder of FIG. 3.

Referring also to FIG. 9, as the actuation assembly 40 moves proximally, the knife 62 of the cutter 60 moves upward through the aperture 44 in the drive bar 42 and upward through a slot 45 in the upper plate 28. This upward motion of the knife 62 may occur substantially as set forth in the Knife Document, and/or in any other suitable manner. The cutting edge 68 encounters and incises tissue adjacent to the upper plate 28. As the actuation assembly 40 continues to move proximally, the knife 62 and cutting edge 68 move proximally as well, incising tissue along the upper plate 28 of the staple holder 24. The knife 62 may be positioned longitudinally in any suitable manner relative to the wedges 50, such that the knife 62 may cut tissue before, during or after staples 4 are sheared off the feeder belt 2 into adjacent tissue.

Referring also to FIG. 5, as the actuation assembly 40 nears the end of its travel, the ramp 43 of the drive bar 42 may encounter the post 36 defined on the lower surface of the stop tab 34. The proximal, free end of the stop tab 34 had previously been located adjacent to a pull tab 6 of at least one feeder belt 2. The ramp 43 is sized such that the stop tab 34 is moved out of engagement with that pull tab 6. As the drive bar 42 continues to move proximally, the post 36 continued to ride on the upper surface of the drive bar 42 distal to the ramp 43, which is shaped and sized to continue to hold the stop tab 34 out of engagement with the pull tab or tabs 6 it had previously engaged.

As the actuation assembly 40 continues to move proximally, the protrusion 74 on the bottom surface of each wedge 50 may approach an aperture 78 defined in a lower surface of the staple holder 24. The aperture 78 may be defined completely through the lower surface of the staple holder 24, or may be a trough or other volume that does not extend through the surface of the staple holder 24. Referring also to FIG. 6, the actuation assembly 40 moves further proximally. The upper surface of the wedge 50 encounters the pull tab 6 to which the stop tab 34 had previously been adjacent. The pull tab 6 is substantially fixed in position vertically. Thus, this contact between the wedge 50 and the pull tab 6 of the corresponding feeder belt 2 causes the wedge 50 to deflect downward. The wedge 50 rotates slightly about the pin 54, causing the wedge arm 52 to bow upward. The proximal end of the wedge arm 52 may be fixed to the corresponding belt support 56, or may be trapped between the belt support 56 and the interior of the staple holder 24 such that the belt support 56 restrains the wedge arm 52 against proximal motion. The protrusion 74 of the wedge 50 is pushed into the aperture 78 as the wedge 50 rotates. The actuation assembly 40 continues to move proximally, and the deflected wedge 50 slides under the pull tab 6. Where the feeder belt 2 includes two rows 8 of staples 4, and two wedges 50 are used to fire those staples 4, each pull tab 6 may extend laterally from both sides of the feeder belt 2, such that a pull tab 6 is in position for each wedge 50 to encounter and deflect downward.

Referring also to FIG. 7, as the actuation assembly 40 continues to move proximally, the wedge 50 moves proximal to the pull tab 6. At that point, the pull tab 6 no longer holds the wedge 50 down, and the wedge 50 is free to move upward behind the pull tab 6 to its original state. The wedge 50 rotates slightly about the pin 54, and the wedge arm 52 straightens back to its initial state. The protrusion 74 of the wedge 50 also moves upward out of the aperture 78. The wedge 50 is, at this point, located behind the corresponding pull tab 6, with the pull tab 6 located lower than the upper surface of the distal end of the wedge 50. The actuation assembly 40 has at this point reached the end of its travel.

The end effector 20 may then be reset. Such resetting may be performed before, during or after the opening of the end effector 20 after its treatment of tissue adjacent to the staple holder 24. The drive bar 42 is advanced distally. As the drive bar 42 is advanced distally, the distal end of each wedge 50 encounters the corresponding pull tab 6. That pull tab 6 is proximal to the staples 4 in the row that were deployed and sheared off the feeder belt 2 during the previous actuation. The distal motion of the wedge 50 pushes that corresponding pull tab 6 distally, thereby pushing the feeder belt 2 to which the pull tab 6 is fixed distally as well. Where two wedges 50 are used to deploy staples 4 in rows 8 on both sides of the feeder belt 2, two wedges 50 each push a side of the pull tab 6 distally, such that the force exerted on the feeder belt 2 is substantially entirely in the distal direction. The wedges 50 continue to push the pull tabs 6 forward, and those pull tabs 6 encounter the tensioning tab 32 in the upper plate 28 of the staple holder 24. That encounter pushes the tensioning tab 32 upward, and the pull tabs 6 move distal to the free end of the tensioning tab 32. Referring also to FIG. 10, at that point, the tensioning tab 32 moves downward, such that the free end of the tensioning tab 32 is adjacent to and proximal to the pull tabs 6. The feeder belt 2 is thus in firing position to deploy the next group 10 of staples 4, and the actuation assembly 40 is in its initial position for the next firing, as is the tensioning tab 32. The wedges 50 are thereby used not only to deploy staples 4 and separate the staples 4 from the feeder belt 2, but also to advance the feeder belt 2 afterward in order to prepare for the next deployment. In this way, the number of parts and the complexity of the tool can be minimized.

Distal travel of the actuation assembly 40 may be limited by the stop tab 34. As the drive bar 42 moves distally, the post 36 of the stop tab 34 rides down the ramp 43 on the upper surface of the drive bar 42, such that the drive bar 42 no longer pushes the stop tab 34 upward out of the way of the pull tabs 6. Distal motion of the feeder belt 2 as pushed distally by the wedges 50 may be stopped by contact between the next most proximal pull tabs 6 and the free end of the stop tab 34. Alternately, distal travel of the actuation assembly 40 is affirmatively controlled by the handle or other component of the surgical stapler. The stop tab 32 is thus back in its initial position.

The cutter 60 is also reset as the actuation assembly 40 moves distally. The cutting edge 68 of the knife 62 is oriented proximally, such that motion of the knife 62 in the distal direction during resetting does not substantially affect tissue, if tissue is still adjacent to the staple holder 24 during reset. The cutter 60 is fixed to the drive bar 42, such that distal motion of the drive bar 42 pushes the cutter 60 distally. As the cutter 60 returns toward its initial position, the knife 62 flexes downward back into the staple holder 24 underneath the upper plate 28, such as set forth in the Knife Document. Alternately, the knife 62 can be returned to its initial position in any suitable manner.

The terms "upper," "lower," "upward," "downward," "up," "down," "below," "above," "vertical," and the like are used solely for convenience in this document; such terms refer to directions on the printed page and do not limit the orientation of the surgical stapler in use. While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. Surgical apparatus, comprising:
a feeder belt;
a plurality of staples frangibly connected to said feeder belt; and
at least one generally polygon-shaped pull tab extending laterally outward from said feeder belt, wherein at least one said pull tab is spaced apart from at least one said staple, and wherein no said pull tab is attached directly to an end of any said staple.

2. The surgical apparatus of claim 1, wherein at least one said pull tab has substantially the same thickness as said feeder belt.

3. The surgical apparatus of claim 1, wherein at least one said pull tab extends in both lateral directions from said feeder belt.

4. The surgical apparatus of claim 1, further comprising at least one wedge slidable relative to said feeder belt.

5. The surgical apparatus of claim 4, further comprising a staple holder into which said feeder belt extends, wherein said staple holder includes a deflectable tensioning tab configured to restrain said feeder belt against proximal motion during distal motion of said wedge against said staples.

6. The surgical apparatus of claim 5, wherein at least one wedge is deflectable downward under at least one pull tab, then deflectable upward proximal to said pull tab such that said wedge is then movable distally to urge said feeder belt distally.

7. The surgical apparatus of claim 6, further comprising a bendable wedge arm extending proximally from said wedge.

8. The surgical apparatus of claim 4, further comprising at least one belt support connected to at least one said wedge.

9. The surgical apparatus of claim 4, further comprising a drive bar connected to at least one said wedge, wherein motion of said drive bar moves said wedge.

10. The surgical apparatus of claim 9, further comprising a flexible cutter fixed to said drive bar.

11. The surgical apparatus of claim 10, wherein said drive bar includes an aperture defined therein to allow at least part of said flexible cutter to move upward therethrough.

* * * * *